United States Patent [19]
Dickens et al.

[11] Patent Number: 5,643,964
[45] Date of Patent: Jul. 1, 1997

[54] NATURAL AMINO ACID DERIVATIVES AS METALLOPROTEINASE INHIBITORS

[75] Inventors: Jonathan Philip Dickens, Cambridge; Michael John Crimmin; Raymond Paul Beckett, both of Cowley, all of England

[73] Assignee: British Biotech Pharmaceuticals Limited, Cowley, United Kingdom

[21] Appl. No.: 374,601

[22] PCT Filed: Jul. 23, 1993

[86] PCT No.: PCT/GB93/01556

§ 371 Date: Jan. 23, 1995

§ 102(e) Date: Jan. 23, 1995

[87] PCT Pub. No.: WO94/02446

PCT Pub. Date: Feb. 3, 1994

[30] Foreign Application Priority Data

Jul. 23, 1992 [GB] United Kingdom ............... 9215665

[51] Int. Cl.$^6$ ............................................. A01N 37/28
[52] U.S. Cl. ................................. 514/575; 562/623
[58] Field of Search ......................... 562/623; 514/575

[56] References Cited

U.S. PATENT DOCUMENTS

| | | | |
|---|---|---|---|
| 3,468,936 | 9/1969 | van der Burg | 260/500.5 |
| 4,996,358 | 2/1991 | Handa et al. | 562/621 |
| 5,183,900 | 2/1993 | Galardy et al. | 548/495 |
| 5,300,674 | 4/1994 | Crimmin et al. | 560/42 |

FOREIGN PATENT DOCUMENTS

| | | |
|---|---|---|
| 0236872 | 9/1987 | European Pat. Off. . |
| 9102716 | 3/1991 | WIPO . |

*Primary Examiner*—Deborah D. Carr
*Attorney, Agent, or Firm*—Hale and Dorr

[57] ABSTRACT

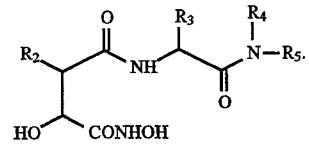

Compounds of Formula (I) wherein $R_2$ represents a group $R_6$—A— wherein A represents a divalent straight or branched, saturated or unsaturated hydrocarbon chain of up to 6 C atoms which may be interrupted by an O or S atom, and $R_6$ represents hydrogen or an optionally substituted phenyl, cycloalkyl or cycloalkenyl group; $R_3$ represents the characterizing side chain of a natural alpha amino acid other than proline, and in which any polar substituents are optionally protected; $R_4$ represents hydrogen or methyl; $R_5$ represents hydrogen, $C_1$–$C_6$ alkyl or a group D-($C_1$–$C_6$ alkyl) wherein D represents hydroxy, ($C_1$–$C_6$)alkoxy, ($C_1$–$C_6$)alkylthio, acylamino, optionally substituted phenyl, or a heterocyclic group, $NH_2$, or a mono- or di-($C_1$–$C_6$ alkyl) amine or a heterocyclic group; or $R_3$ and $R_5$ taken together represent a divalent, saturated or unsaturated hydrocarbon chain of from 8–14 C atoms, which may be interrupted by an O, S or N heteroatom, or a salt, solvate or hydrate thereof.

11 Claims, No Drawings

NATURAL AMINO ACID DERIVATIVES AS METALLOPROTEINASE INHIBITORS

This application is a 371 of PCT/GB93/01556 filed Jul. 23, 1993.

The present invention relates to therapeutically active hydroxamic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and turnour metastasis, invasion and growth.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses. similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these turnours.

Compounds which inhibit the production or action of TNF are therefore thought to be potentially useful for the treatment or prophyiaxis of many inflammatory, infectious, immunological or malignant diseases. These include, but are not restrictecd to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rneumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Several classes of MMP inhibitors have been proposed, including derivatives of hydroxamic acid. The following patent publications disclose hydroxamic acid-based MMP inhibitors:

U.S. Pat. No. 4,599,361 (Searle)
EP-A-0236872 (Roche)
EP-A-0274453 (Bellon)
WO 90/05716 (British Bio-technology)
WO 90/05719 (British Bio-technology)
WO 91/02716 (British Bio-technology)
EP-A-0489577 (Celltech)
EP-A-0489579 (Celltech)
EP-A-0497192 (Roche)
WO 92/13831 (British Bio-tecnnology)
WO 92/22523 (Research Corporation Technologies)
WO 93/09090 (Yamanouchi)

The intrinsic potency of compounds within the broad structural groups of hydroxamic derivatives disclosed in the above publications against particular MMPs can be high. For example. many have a coliagenase $IC_{50}$ by the in vitro test method of Cawston and Barrett, (Anal. Blochem., 99, 340–345, 1979) of less than 50 nM. Unfortunately. bowever, the physiochemical and/or pharmacokinetic properties of the specific compounds dislosed in those publications have generally been disappointing. Identifying hydroxamic acid-based MMP inhibitors having a good balance of high intrinsic activity against the target MMPs, and good physicochemical and/or pharmacokinetio properties, such that the compounds are easily formulated for administration, have good bibavailability for acceptable periods following administration, and have high in vivo activity in the target disease or condition, remains a much sought after goal in the art.

The above patent publications disclose nothing concerning the inhibition of TNF release. Indeed it appears that the state of the art as a whole does not include the recognition of anti-TNF properties in any MMP-inhibiting hydroxamic acid derivatives.

The hydroxamic acid derivatives disclosed in the above publications can be regarded as having the following basic structure (IA):

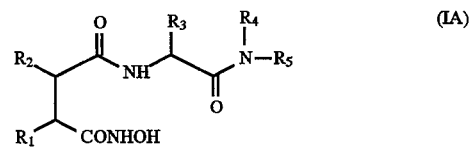

wherein the five substituents $R_1$–$R_5$ may vary according to the detailed disclosure of each publication. The balance of intrinsic level of activity, degree of specificity of inhibition of particular categories of MMP, physicochemical and pharmacokinetic properties can vary in an unpredictable way as the substituents $R_1$–$R_5$ are varied.

Of the above publications, only EP-A-0236872 refers to the possibility that in a particular class of collagenase inhibitors of basic structure (IA) the substituent $R_1$ may be OH. That possibility is referred to amongst many other possible $R_1$ substituents, in the context of compounds in which the substituent $R_3$ is the characteristic side chain of a naturally occurring amino acid in which any functional substituents may be protected. any amino group may be acylated, and any carboxyl group may be esterified. EP-A-0236872 does not disclose such compounns as having preferred or particularly advantageous collagenase inhibitory properties, and in fact contains no disclosure of any specific compound in which $R_1$ is hydroxy. It does not address the problem in the art referred to above of providing hydroxamic acid derived MMP inhibitors having the elusive balance of good intrinsic activity profile ancl good physicochemical and pharmacokinetic properties.

This invention is based on the finding that a specific sub-group of compounds within the group generically disclosed in EP-A-0236872 have in general the sought after but unpredictable combination of desirable formulation characteristics. including good water-solubility, as well as desirable activity profiles as inhibitors of MMP's, including both coltagenase and stromelysin inhibitory activity. That subgroup is principally characterised in that the $R_1$ substituent is a hydroxy group and the substituent $R_3$ is the side chain of a natural amino acid which either contains no polar groups or in which any such polar groups are protected. The selected sub-group of the invention includes compounds which achieve high serum levels following oral administration, and which are activo in vive following oral administration in relevant animal models of diseases and conditions mediated by MMP's. Furthermore, as mentioned above, compounds of the invention have been found to have the unexpected and desirable property of inhibiting TNF production.

According to one aspect of the present invention, there is provided a compound of formula (I):

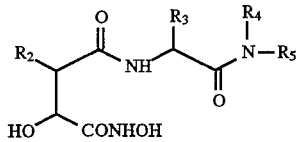

wherein
- $R_2$ represents a group $R_6$—A— wherein A represents a divalent straight or branched, saturated or unsaturated hydrocarbon chain of up to 6 C atoms which may be interrupted by an O or S atom, and $R_6$ represents hydrogen or an optionally substituted phenyl, cycloalkyl or cycloalkenyl group;
- $R_3$ represents the cnaracterising side chain of a natural alpha amino acid other than proline, and in which any polar substituents are optionally protected;
- $R_4$ represents hydrogen or methyl;
- $R_5$ represents hydrogen, $C_1$–$C_6$ alkyl or a group D-($C_1$–$C_6$ alkyl) wherein D represents hydroxy, ($C_1$–$C_6$)alkoxy, ($C_1$–$C_6$)alkylthio, acylamino, optionally substituted phenyl, or a heterocyclic group, $NH_2$, or a mono- or di-($C_1$–$C_6$ alkyl) amine or a heterocyclic group;
- or $R_3$ and $R_5$ taken together represent a divalent, saturated or unsaturated hydrocarbon chain of from 8 to 16 C atoms, which may be interrupted by an O, S or N heteroatom, or a salt, solvate or hydrate thereof.

As used herein the term "$C_1$–$C_6$ alkyl" or "saturated hydrocarbon chain of up to 6 C atoms" refers to a straight or branched chain alkyl moiety having from 1 to 6 carbon atoms, including for example, methyl, ethyl, propyl, isopropyl, butyl, t-butyl, pentyl and hexyl.

The term "$C_2$–$C_6$ alkenyl" or "unsaturated hydrocarbon chain of up to 6 C atoms" refers to a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

The term "cycloalkyl" refers to a saturated alicyclic moiety having from 3–8 carbon atoms and includes, for example, cyclohexyl, cyclooctyl, cycloheptyl, cyclopentyl, cyclobutyl and cyclopropyl.

The term "cyctoalkenyl" refers to an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon atoms, the ring may contain more than one double bond.

The term "heterocyclyl" or "heterocyclic" refers to a 5–7 membered heterocyclic ring containing one or more heteroatoms selected from S, N and O, and optionally fused to a benzene ring, including for example, pyrolyl, furanyl, thienyl, imidazolyl, oxazolyl, thiazolyl, pyrazolyl, pyridinyl, pyrrolidinyl, pyrimidinyl, morpholinyl, piperizinyl, indolyl and benzimidazole.

Unless otherwise specified in the context in which it occurs, the term "substituted" as applied to any moiety herein means substituted with up to four substituents, each of which independently may be $C_1$–$C_6$ alkoxy, hydroxy, thio, $C_1$–$C_6$ alkylthio, amino, halo (including fluoro, chloro, bromo and iodo), trifluoromethyl, nitro, —COOH, —$CONH_2$ or —$CONHR^4$ wherein $R^4$ is a $C_1$–$C_6$ alkyl group or the residue of a natural alpha-amino acid.

The term "characteristic side chain of a natural alpha-amino acid" means the characteristic side chain attached to the —$CH(NH_2)(COOH)$— moiety in the following amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

Natural alpha-amino acids which contain polar substituents (by which is meant amino, carboxyl, hydroxy, mercapto, guanidyl, imidazolyl, or indolyl) in their characteristic side chains are arginine, lysine, glutamic acid, aspartic acid, tryptophan, histidine, serine, threonine, tyrosine, and cysteine. When $R_3$ in the compounds of the invention is one of those side chains, the polar substituent may optionally be protected.

The term "protected" when used in relation to an amino, carboxyl or polar substituent in a side chain of a natural alpha-amino acid means a derivative of such a substituent which is sulastantially non-polar. In this context, protected amino groups include amido and acylamino, protected hydroxy or mercapto groups include ethers and thioethers, protectecl carboxyl groups include esters, and imidazolyl, indolyl or guanidyl groups may be protected as t-butoxycarbonyl derivatives. These are only examples of the many protecting derivatives known in the art, and others will be known to the skilled man.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartates, fumarates and maleates. Salts may also be formed with bases, for example sodium, potassium. magnesium. and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:
- C atom carrying the hydroxy group and hydroxamic acid moiety—S.
- C atom carrying the $R_2$ group—R,
- C atom carrying the $R_3$ group—S, but mixtures in which the above configurations predominate are also contemplated.

In the compounds of the invention:
- $R_2$ may for example be a $C_3$–$C_6$ alkyl, cycloalkyl($C_3$–$C_6$ alkyl), phenyl($C_2$–$C_6$ alkyl), $C_2$–$C_4$ alkoxy($C_1$–$C_3$ alkyl)$_m$, or $C_2$–$C_4$ alkylsulphanyl($C_1$–$C_3$ alkyl)$_m$ group wherein is 0 or 1. Examples of particular $R_2$ groups include iso-butyl, n-pentyl, cyclohexylpropyl, cyclohexylbutyl, cyclohexylpentyl, phenylethyl, phenylpropyl, phenylbutyl, phenylpentyl, propytoxymethyl, and propytsulphanyl. Presently preferred are compounds in which $R_2$ is iso-butyl;

$R_3$ may for example be the characterising side chain of phenylalanine, valine, leucine, isoleucine, methionine, giycine, asparagine, glutamine, or alanine: or the characterising side chain of cysteine, tyrosine, tryptophan, histidine, serine, threonine, arginine, glutamic acid, lysine, or aspartic acid in which the polar groups therein are optionally protected. Presently preferred are compounds in which $R_3$ is phenylmethyl—the characteristic side chain of phenylalanine.

$R_4$ may for example be hydrogen, methyl or ethyl. Presently preferred are compounds in which $R_4$ is hydrogen;

$R_5$ may for example be hydrogen or $C_1$–$C_4$ alkyl, or a group D-($C_1$–$C_6$ alkyl) wherein D represents hydroxy, ($C_1$–$C_6$)alkoxy, ($C_1$–$C_6$)alkylthio, acylamino, optionally substituted phenyl, or a heterocyclic group. Examples of particular $R_5$ groups include methyl, ethyl, propyl, butyl, hydroxyethyl, 2-ethylthioethyl, 2-acetoxyethyl, N-acetyl-2-aminoethyl, 3-(2-pyrrolidone)propyl, optionally substituted phenylethyl, phenytpropyl, phenylbutyl and phenylpentyl, Presently preferred are compounds in which $R_5$ is methyl or ethyl.

Interesting compounds of the invention are:

$N^2$-[3S-Hydroxy-4-(N-hydroxyamino)-2R-isobutylsuccinyl)]-L-leucine-$N^1$-methylamide; and $N^2$-[3S-Hydroxy-4-(N-hydroxyamino)-2R-isobutylsuccinyl)]-5-methyl-L-glutamic acid-$N^1$-methylamide;

and salts, solvates or hydrates thereof.

A compound of the invention which is presently especially preferred for its balance of good formulation characteristics such as water solubility, high intrinsic activity in inhibiting collagenase and stromelysin. activity in inhibiting TNF release, and good pharmacokinetic properties. evidenced for example by high in vivo activity following oral administration in the standard rat adjuvant arthritis model, is:

$N^2$-[3S-Hydroxy-4-(N-hydroxyamino)-2R-isobutylsuccinyl)]-L-phenylalanine-$N^1$-methylamide and salts, solvates or hydrates thereof.

Compounds according to the present invention may be prepared by methods known per se in the art, and by the following process, which forms another aspect of the invention, namely a process for the preparation of a compound of formula (I) comprising:

(a) coupling an acid of general formula (II)

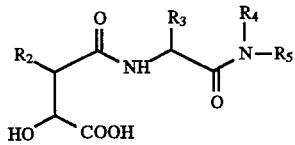

or an activated derivative thereof with hydroxylamine, O-protected hydroxylamine, or a salt thereof, $R_2$, $R_3$, $R_4$, and $R_5$ being as defined in general formula (I) except that any substituents in $R_2$, $R_3$, $R_4$, and $R_5$ which are potentially reactive with hydroxylamine, O-protected hydroxylamine or their salts may themselves be protected from such reaction, then removing any protecting groups from the resultant hydroxamic acid moiety and from any protected substituents in $R_2$, $R_3$, $R_4$, and $R_5$; and (b) optionally convening a compound of general formula (I) into another compound of general formula (I).

Conversion of (II) to an activated intermediate such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (WSCDI), or 2-ethoxy-1-ethoxycarbonyl-1,2-dihydroquinoline (EEDQ).

Protecting groups as referred to above process are well known per se, for example from the techniques of peptide chemistry. Amino groups are often protectable by acyl groups, for example benzyloxycarbonyl, t-butoxycarbonyl or acetyl groups, or in the form of a pnthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

A compound of general formula (II) can be prepared by coupling an acid of formula (III) or an activated derivative thereof with an amine of formula (IV)

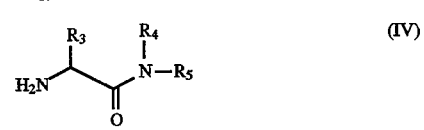

wherein $R_2$, $R_3$, $R_4$, and $R_5$ are as defined in general formula (I) and $R_{10}$ and $R_{11}$ separately represent hydroxy protecting groups or taken together represent a divalent moeity which simultaneously protects both hydroxy groups, and subsequently removing the protecting groups or protecting moeity. Active derivatives of acids (III) include activated esters such as the pentafluorophenyl ester, acid anhydrides and acid halides, eg chlorides. $R_{10}$ and $R_{11}$ may be any of the standard hydroxyl protecting groups known in the art, but a particularly useful technique may be simultaneous protection of the two hydroxy groups as a dioxalone of formula (V):

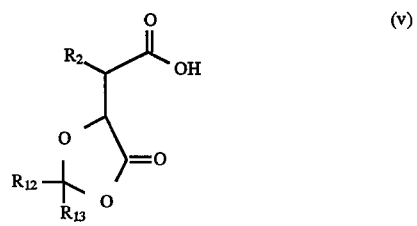

wherein the groups $R_{12}$ and $R_{13}$ are derived from a dioxalone forming reagent, and may be, for example, hydrogen, alkyl, phenyl or substituted phenyl.

As mentioned above, compounds of formula (I) are useful in human or veterinary medicine since they are active as inhibitors of MMPs, and a further advantage lies in their ability to inhibit the release of tumour necrosis factor (TNF) from cells.

Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMPs and/or TNF; and (iii) the use of a compound as defined with respect to formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compouna of formula (I) together with a pharmaceutically or veterinariiy acceptable excipient or carrier. In view of the water-solubility, and oral bioavailability advantanges of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parentera solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica: disintegrants for example potato starch, or acceptable wetting agents such as sodium iauryi sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitoi, syrup, methyl cellulose, glucose syrup, gelatin hydrogenareal edible fats; emulsifying agents, for example lecithin, sorbitan monocleate, or acacia: non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following Examples illustrate embooiments of the invention:

The amino acids used in the examples below were commercially available or were prepared according to literature procedures. In all cases these were converted to the required N-methylamides by standard methods.

EXAMPLE 1

$N^2$-[3S-Hydroxy-4-(N-hydroxyamino)-2R-isobutylsuccinyl)]-L-phenylalanine-$N^1$-methylamide

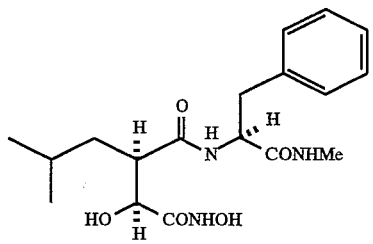

EXAMPLE 1a

Isopropyl 3R-carboxyisopropyl-2S-hydroxy-5-methylhex-5-enoate

Diisopropyl-2S-hydroxybutanedioate (50 g, 230 mmol) was added to a solution of lithium N,N-diisopropylamide [from N,N-diisopropylamine (80 ml, 570 mmol) and 10M n-butyllithium (48.1 ml, 481 mmol)] in dry tetrahydrofuran (500 ml) whilst maintaining the temperature at −70° C. When addition was complete the reaction was warmed to −15° C. and stirred for 8 hours. The reaction mixture was cooled to −70° C. and methallyl iodide (46 g, 252 mmol) was added slowly, ensuring that the temperature did not exceed −65° C. The mixture was warmed to −40° C. and stirred for 18 hours before quenching at −15° C. with citric acid. The organic layer was separated and washed with 10% sodium bicarbonate solution (500 ml) and brine (300 ml) then dried over magnesium sulphate. The solution was filtered and concentrated in vacuo to give a brown oil (64 g) which was purified by column chromatography (silica gel, 1 kg, gradient elution with 20 to 35% diethyl ether in hexane). The desired product was isolated as a colourless oil (30.9 g. 49%) which was found to be a 17:1 mixture of diastereomers by NMR. $^1$H-NMR; δ (Chloroform-d, major diastereomer), 5.06 (1H, septet. J=6.3 Hz), 4.97 (1H, septet. J=6.3 Hz). 4.78 (2H, d, J=7.1 Hz), 4.16 (1H, m), 3.20 (1H, d, J=6.2 Hz), 3.00 (1H, m), 2.50, 2.35 (2H, ABX, J=7.0, 8.7, 14.4 Hz), 1.72 (3H, s) and 1.24–1.16 (12H, 2m).

EXAMPLE 1b

Isopropyl 3R-carboxyisopropyl-2S-hydroxy-5-methylhexanoate

Isopropyl 3R-carboxyisopropyl-2S-hydroxy-5-methylhex-5-enoate (7.14 g, 26.2 mmol) was dissolved in ethanol (80 ml), and stirred overnight with 10% palladium on charcoal catalyst (1.0 g) under an atmosphere of hydrogen. The catalyst was removed by filtration and the filtrate was evaporated to dryness to leave the product as a clear oil (7.03 g, 98%). $^1$H-NMR; δ (Chloroform-d), 5.06 (1H, septet, J=6.3 Hz), 4.97 (1H, septet, J=6.3 Hz), 4.17 (1H, br s,), 3.24 (1H, br s), 2.83 (1H, m), 1.68 (2H, m), 1.44 (1H, m), 1.24 (6H, d, J=6.2 Hz), 1.18 (6H, d, J=6.2 Hz) and 0.89 (6H, m).

EXAMPLE 1c

3R-Carboxy-2S-hydroxy-5-methylhexanoic acid

Isopropyl 3R-Carboxyisopropyl-2S-hydroxy-5-methylhexanoate (7.0 g, 25.6 mmol) was dissolved in dioxane (15 ml) and water (15 ml), a solution of potassium hydroxide (4.29 g) in water (22 ml) was added and the mixture was heated at 90° C. overnight. The solution was allowed to cool and then passed through an ion exchange resin (Dowex 50X4-400, 200 ml) to yield the title compound (4.82 g, 99%). $^1$H-NMR; δ (Chloroform-d), 8.70 (2H, br s), 4.32 (1H, br s), 3.10 (1H, m), 1.85–1.55 (3H, m) and 0.96 (6H, m).

EXAMPLE 1d 2R-(2,2-Dimethyl-4-oxo-1,3-dioxaian-5S-yl)-4-methylpentanoic acid 3R-Carboxy-2S-hydroxy-5-methylhexanoic acid (5.19 g. 27.3 mmol) was dissolved in 2,2-dimethoxypropane (150 ml) and N,N-dimethylformamide (40 ml) and stirred overnight at 30° C. in the presence of a catalytic amount of p-toluene sulphonic acid. The solvent was removed to give the title compound contaminated with solvent (6.87 g, >100%). $^1$H-NMR: δ (Chloroform-d), 4.41 (1H, d, J=4.8 Hz), 2.91 (1H, m), 1.69 (3H, m), 1.54 (3H, s), 1.48 (3H, s) and 0.88 (6H, m).

EXAMPLE 1e

Pentafluorophenyl 2R-(2,2-Dimethyl-4-oxo-1,3-dioxalan-5S-yl)-4-methyl pentanoate 2R-(2,2-Dimethyl-4-oxo-1,3-dioxaian-5S-yl)-4-methylpentanoic acid (558 mg, 2.4 mmol) was taken up in dichloromethane (10 ml) and cooled to 0° C. before adding pentafluorophenol (670 mg, 3.6 mmol) and N-ethyl-N'-(3-dimethylaminopropyl) carbodiimide (560 mg, 2.9 mmol). The reaction was stirred at 0° C. for 2 hours then the solution was washed with 1M sodium carbonate (50 ml) and brine (20 ml). The organic layer was dried (magnesium sulphate), filtered, evaporated to dryness and purified by column chromatography (silica gel, dichloromethane) to give the activated ester (552 mg, 58%). $^1$H-NMR; δ (Chloroform-d), 4.57 (1H, d, J=6.5 Hz), 3.32 (1H, m), 1.86 (3H, m), 1.67 (3H, s), 1.58 (3H, s) and 1.03 (6H, m).

EXAMPLE 1f $N^2$-[2R-(2,2-Dimethyl-4-oxo-1,3-dioxaian-5S-yl)-4-methylpentanoyl]-L-phenylalanine-$N^1$-methylamide Pentafluorophenyl 2R-(2,2-dimethyl-4-oxo-1,3-dioxalan-5S-yl)-4-methyl pentanoate (24 g, 60.6 mmol) and L-phenylalanine-N-methylamide (11.87 g. 66.7 mmol) were dissolved in N,N-dimethylformamide (250 ml) and the mixture was stirred for 40 hours at 30° C. The solvent was removed under reduced pressure and the residue was dissolved in dichloromethane (250 ml), washed with 1M sodium carbonate (2×250 ml) and brine (250 ml) and dried (magnesium sulphate). The solution was filtered and evaporated to a white solid which was recrystallised from ethyl acetate—hexane (11.91 g, 51%). $^1$H-NMR; δ (Chloroform-d), 7.27 (5H, m), 6.54 (1H, br d, J=7.9 Hz), 6.13 (1H, br m), 4.65 (1H, m), 4.52 (1H, d, J=5.4 Hz), 3.10 (2H, d, J=7.1 Hz), 2.71 (4H, m and d. J=4.8 Hz), 1.54 (3H, s), 1.52 (5H, s and m) 1.39 (1H, m) and 0.85 (6H, 2d).

EXAMPLE 1g $N^2$-[3S-Hydroxy-4-hydroxy-2R-isobutylsuccinyl)]-L-phenylalanine-$N^1$-methylamide.

$N^2$-[2R-(2,2-Dimethyl-4-oxo-1,3-dioxalan-5S-yl)-4-methylpentanoyl]-L-phenylalanine-$N^1$-methylamide (11.90 g, 30.5 mmol) was dissolved in tetrahydrofuran (175 ml) and cooled to 4° C. during the addition of 2M hydrochloric acid (175 ml). The solution was allowed to warm to room temperature and then stirred for 18 hours. The bulk of the solvent was removed under reduced pressure before drying under high vaccuum to an off-white foam (10.79 g, ca. quant.). $^1$H-NMR; δ (Methanol-$d_4$), 7.19 (5H, m), 4.53 (1H, m), 4.13 (1H, d, J=5.0 Hz), 3.18, 2.90 (2H, ABX, J=5.5, 9.1, 13.9 Hz), 2.66 (4H, s and m), 1.49 (1H, m), 1.23 (2H, m), 0.78 (3H, d, J=6.0 Hz) and 0.75 (3H, d, J=6.0 Hz).

EXAMPLE 1h $N^2$-[4-(N-Benzyioxyamino)-3S-Hydroxy-2R-isobutylsuccinyl)]-L-phenylalanine-$N^1$-methylamide.

To a solution of $N^2$-[3S-hydroxy-4-hydroxy-2R-isobutylsuccinyl)]-L-phenylalanine-N $^1$-methylamide (10.79 g, 30.8 mmol) in tetrahydrofuran (200 ml) was added added O-benzylhydroxylamine hydrochloride (7.38 g, 46.2 mmol: 1.5 eq.) in water (150 ml). The solution was cooled to 0° C. before addition of N-ethyl-N'-(3-dimethylaminopropyl)carbodiimide hydrochloride (11.82 g, 61.7 mmol; 2 eq.) in water (50 ml); the product began to crystallise from solution after approximately 10 minutes. The reaction mixture was allowed to warm to room temperature then stirred overnight. The product was collected by filtration, washed with water then diethyl ether and dried to constant weight under high vaccuum (11.43 g, 81%). $^1$H-NMR; δ (Methanol-$d_4$), 7.31 (5H, m, Ph), 7.19 (5H, m), 4.80 (2H, s; under H$_2$O peak), 4.52 (1H, dd, J=6.1, 8.5 Hz), 3.98 (1H, d, J=5.4 Hz), 3.12, 2.91 (2H, ABX, J=6.1, 8.7, 13.8

Hz), 2.64 (3H, s), 2.59 (1H, m,), 1.42 (1H, m), 1.23 (1H, m), 1.13 (1H, m), and 0.78, 0.75 (6H, 2d, J=6.4 Hz).

EXAMPLE 1i $N^2$-[3S-Hydroxy-4-(N-hydroxyamino)-2R-isobutylsuccinyl)]-L-phenylalanine-$N^1$-methylamide.

$N^2$-[4-(N-Benzyloxyamino)-3S-hydroxy-2R-isobutylsuccinyl)]-L-phenylalanine-$N^1$-methylamide (11.43 g, 25.1 mmol) was dissolved in ethanol (125 ml) and methanol (375 ml) and stirred with 10% palladium on charcoal (1.5 g) under an atmosphere of hydrogen until TLC showed that the debenzylation was complete (4.5 hours). The catalyst was removed by filtration and the solvent evaporated to leave a white solid which was dried to constant weight under high vaccuum (7.51 g, 85%). $^1$H-NMR; δ (Methanol-$d_4$), 7.19 (5H, m, Ph), 4.50 (1H, dd, J=6.2, 8.6 Hz), 3.99 (1H, d, J=5.7 Hz), 3.14, 2.92 (2H, ABX, J=6.3, 8.7, 13.9 Hz), 2.65 (3H, s), 2.58 (1H, m,), 1.48 (1H, m), 1.12 (2H, m), and 0.77, 0.74 (6H, 2d, J=6.2, 6.3 Hz), $^{13}$C-NMR; δ (Methanol-$d_4$), 175.5, 173.9, 171.5, 138.6, 130.2, 129.5, 127.8, 72.7, 56.2, 49.8, 39.3, 38.7, 26.6, 26.3, 23.7 and 22.1. Found: C. 57.93. H, 7.48. N. 11.58%: $C_{18}H_{27}N_3O_5 \cdot 0.4H_2O$ requires: C. 58.02, H, 7.52, N, 11.28%.

EXAMPLE 2

$N^2$-[3S-Hydroxy-4-(N-hydroxyamino)-2R-isobutylsuccinyl)]-L-leucine-$N^1$-methylamide

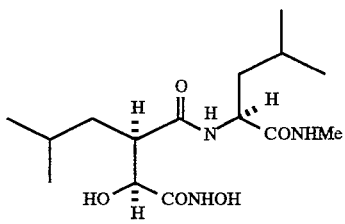

Prepared in a manner analogous to that described in example 1, from L-leucine-N-methylamide. $^1$H-NMR; δ (Methanol-$d_4$), 4.34 (1H, dd, J=5.5, 9.3 Hz), 3.98 (1H, d, J=6.3 Hz), 2.68 (4H, s and m), 1.66 (5H, m), 1.21 (1H, m), 0.89 (12H, m), $^{13}$C-NMR; δ (Methanol-$d_4$), 175.7, 175.2, 171.5, 73.0, 53.1, 41.9, 39.2, 26.9, 26.3, 25.8, 23.7, 23.5, 22.2 and 21.8.

EXAMPLE 3

$N^2$-[3S-Hydroxy-4-(N-hydroxyamino)-2R-isobutylsuccinyl)]-5-methyl-L-glutamic acid-$N^1$-methylamide

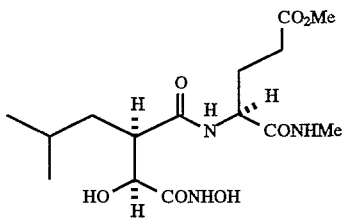

Prepared in a manner analogous to that described in example 1, from 5-methyl-L-glutamic acid-N-methylamide. $^1$H-NMR; δ (Methanol-$d_4$), 4.32 (1H, q, J=4.9, 9.3 Hz), 3.97 (1H, d, J=6.8 Hz), 3.62 (3H, s), 2.72 (1H, m), 2.69 (3H, s), 2.38 (2H, m), 2.08 (1H, m), 1.89 (1H, m), 1.54 (2H, br m), 1.17 (1H, m) and 0.90.0.87 (6H, 2d, J=6.6 Hz). Found: C, 48.91, H, 7.29, N, 11.39%: $C_{15}H_{27}N_3O_7 \cdot 0.4H_2O$ requires: C, 48.88, H, 7.60, N, 11.40%.

Biological Example A

The potency of compounds of the invention to act as inhibitors of collagenase was determined by the procedure of Cawston and Barrett. (*Anal. Biochem.*, 99, 340–345, 1979), hereby incorporated by reference. whereby a 1 mM solution of the compound being tested, or a dilution thereof, was incubated at 37° for 16 hours with collagen and collagenase (buffered with 25mM Hepes, pH 7.5 containing 5 mM $CaCl_2$, 0.05% Brij 35 and 0.02% $NaN_3$). The collagen was acetylated $^{14}$C collagen prepared by the method of Cawston and Murphy, (*Methods in Enzymology*, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity ($IC_{50}$).

The potency of compounds of the invention to act as inhibitors of stromelysin was determined by the procedure of Cawston et al, (*Biochem, J.*, 195, 159–165, 1981), hereby incorporated by reference, whereby a 1 mM solution of the compound being tested, or a dilution thereof, was incubated at 37° for 16 hours with stromelysin and $^{14}$C acetylate casein (buffered with 25 mM Hepes, pH 7.5 containing 5 mM $CaCl_2$, 0.05% Brij 35 and 0.02% $NaN_3$). The casein was acetylareal $^{14}$C casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity ($IC_{50}$).

In the following results the potencies of the compounds of examples 1,2 and 3 above in the above tests are compared in the same tests with the products of examples 13 and 27 of EP-A-236872 (Roche), namely:

[4-(N-hyaroxyamino) 2(R)-isobutylsuccinyl)]-L-leucyl-L-alanine ethyl ester, and

[4-(N-hydroxyamino) 3(S)-phthaloylaminobutyl-2(R)-isobutylsuccinyl)]-L-leucylglycyl ethyl ester.

The former compound (hereafter referred to as C1) was chosen for comparison because of the collagenase inhibitors whose activity is reported in EP-A-236872, it is the most active. The latter compound (hereafter referred to as C2) was chosen for comparison because of the collagenase inhibitors whose activity is reported in EP-A-236872, it is the only one with a substituent in the position equivalent to the hydroxy substituent of the compounds of this invention.

Results:

| Compound  | Collagenase IC50 | Stromelysin IC50 |
| --------- | ---------------- | ---------------- |
| Example 1 | 9                | 150              |
| Example 2 | 8                | 90               |
| Example 3 | 30               | 400              |
| C1        | 15               | 300              |
| C2        | 7                | 70               |

Biological Example B

The concentration over time of compounds of the invention in the blood of laboratory animals following administration of the test compounds was measured.

Test compounds were administered by gavage to 6 male rats (300 g) per treatment group. Blood samples were removed by tail venepuncture at 0.5, 1.0, 2.0, 6.0 and 24 hours post administration. 0.4 ml of blood was placed into 4.5 ml tubes containing 0.1 ml acid citrate dextrose (ACD) as anti-coagulant. For extraction, 3 ml methanol was added and the precipitated blood pelletted by centrifugation (30 min at 3000 rpm). A 2 ml aliquot of supernatant was removed and concentrated by lyophilisation. The extract was redissolved in 200 µl DMSO and a 10 µl aliquot assayed for collagenase inhibitory activity. The inhibitory activity in the extracts was determined using the collagenase assay described in Biological Example A above, and the concentration of inhibitor (that is drug plus any active metabolites) obtained by comparison with standard curves. Results are expressed as peak concentration in ng/ml, as area under the curve (AUC) in ng/ml×hours, over 0–6 hours, and as AUC in number of $IC_{50}$'s×hours.

The compound of example 1 above was compared with the comparison compounds C1 and C2.

Results

| Compound | Peak conc ng/ml | AUC (0–6 h) ng/ml × h | AUC (0–6 h) n $IC_{50}$'s × h |
|---|---|---|---|
| Example 1* | 75.5 @ 0.5 h | 253.8 | 42.6 |
| C1 | 25 @ 0.5 h | 91.7 | 7.4 |
| C2 | 1 @ 1 h | 5.3 | 2.12 |

*average of two results

Biological Example C

The activities of the compound of example 1 above and comparison compound C1 (see Biological Example A above) were assessed in an adjuvant-induced arthritis model.

Adjuvant arthritis was produced in male Lewis rats (Charles River) by a single intradermal injection of 0.75 mg of *M. butyricum* in light paraffin oil (Freunds complete adjuvant—FCA) into the base of the tail. The "secondary" lesion occurs after a delay of 10 days, and is characterised by inflammation of the hindpaws. Hindpaw edemia volumes were measured plethysmographically by water displacement. The test compound was dosed b.i.d. from days 13 to 17. Paw volume on day 20 was measured and compared to that on day 13. The experiment was terminated on day 23.

On day 20, the compound of example 1 (dosed at 10 mg/kg) showed a statistically significant (p<0.01) reduction in swelling relative to control, whereas compound C1 had no effect.

Biological Example D

The ability of compounds of the invention to inhibit the release of TNF was investigated. The assay is based on the ability of phorbol myristate acetate (PMA) to stimulate the release of TNF α from a human monocytic cell line, U937. U937 cells cultured in RPMI 1640 medium+5% foetai calf serum are centifuged at 1000×g for 5 minutes and then resuspended in medium at 2×10⁶/ml. 1 ml of cell suspension is aliquoted into individual wells of 24-well plates. Test compounds are dissolved in dimethyl sulphoxide (DMSO) at a stock concentration of 100 mM, then diluted to 50× the final required concentration with RPMI 1640 medium. 20 µl of the diluted compounds are added to U937 cells in duplicate wells. TNF α release is stimulated by addition of PMA to tine cells at a final concentration of 50 nM.

Appropriate control cultures are set up in duplicate. The plates are incubated for 18 hours at 37° C. 5% $CO_2$, then centrifuged at 1000×g for 5 minutes. A specific ELISA for TNF α obtained from British Bio-technology Products Limited. Abingdon, England is used to measure TNF α levels in the culture supernatants The average concentration of test compound which inhibits the release of TNF α by 50% relative to the control culture was assessed. The compounds of examples 1 and 3 above were tested and had $IC_{50}$ values less than 50 µM.

Aqueous Solubility Example

The solubilities of compounds of the invention in water at ambient temperature were measured, and compared with comparison compounds C1 and C2 (identified in Biological Example A above).

Results:

| Compound | Solubility mg/ml |
|---|---|
| Example 1 | 1.8 |
| Example 2 | 2.09 |
| Example 3 | 3 |
| C1 | 0.3 |
| C2 | <0.1 |

We claim:

1. A compound of formula (I):

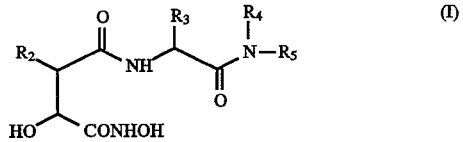

wherein

R2 is $C_3$–$C_6$ alkyl;

R3 is the characterizing side chain of phenylalanine, valine, leucine, isoleucine, methionine, glycine, asparagine, glutamine, or alanine; or the characterizing side chain of cysteine, tyrosine, tryptophan, histidine, serine, threonine, arginine, glutamic acid, lysine, or aspartic acid in which the polar groups therein are optionally protected.

R4 is hydrogen; and

R5 is methyl or ethyl.

2. A compound of formula (I):

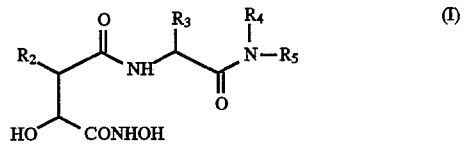

R2 is isobutyl;

R3 is the characterizing side chain of phenylalanine, namely phenylmethyl;

R4 is hydrogen; and

R5 is methyl.

3. $N^2$-[3S-Hydroxy-4-(N-hydroxyamino)-2R-isobutylsuccinyl)]-L-phenylalanine-$N^1$-methylamide, or a salt, solvate or hydrate thereof.

4. A pharmaceutical composition comprising the compounds of claim 2 or claim 3 and a pharmaceutically or veterinarily acceptable excipient or carrier.

5. A method of inhibiting MMP activity in a patient in need thereof comprising administering an effective amount of the compounds of claim 2 or claim 3.

6. A method of inhibiting TNF activity in a patient in need thereof comprising administering an effective amount of the compounds of claims 2 or claim 3.

7. The pharmaceutical composition of claim 3 wherein said pharmaceutical composition is administered orally.

8. The method of claim 5, wherein said MMP activity is the result of a patient suffering from rheumatoid arthritis, osteoarthritis, periodontitis, gingivitis, corneal ulceration or tumor invasion by secondary metastases.

9. The method of claim 5, wherein said compounds are administered as a prophylaxis for MMP activity.

10. The method of claim 6, wherein inhibiting said TNF activity is the result of a patient suffering from inflammation, fever, cardiovascular effects, hemorrhage, coagulation and acute phase response, cachexia and anorexia, an acute infection, a shock state, a graft versus host reaction, or autoimmune disease.

11. The method of claim 6, wherein said compounds are administered as a prophylaxis for TNF activity.

* * * * *